United States Patent
Doerr (10) Patent No.: US 8,682,427 B2
(45) Date of Patent: Mar. 25, 2014

(54) SINGLE-CHAMBER HEART STIMULATOR

(75) Inventor: Thomas Doerr, Berlin (DE)

(73) Assignee: Biotronik CRM Patent AG (CH)

( * ) Notice: Subject to any disclaimer, the term of this patent is extended or adjusted under 35 U.S.C. 154(b) by 699 days.

(21) Appl. No.: 12/575,499

(22) Filed: Oct. 8, 2009

(65) Prior Publication Data

US 2010/0114213 A1 May 6, 2010

(30) Foreign Application Priority Data

Nov. 5, 2008 (DE) .......... 10 2008 043 480

(51) Int. Cl.
*A61N 1/36* (2006.01)

(52) U.S. Cl.
USPC .......................................................... 607/5

(58) Field of Classification Search
CPC ........ A61N 1/36; A61N 1/362; A61N 1/3621
See application file for complete search history.

(56) References Cited

U.S. PATENT DOCUMENTS

| | | | |
|---|---|---|---|
| 4,091,417 A | 5/1978 | Nieson | |
| 5,354,316 A | 10/1994 | Keimel | |
| 6,101,417 A | 8/2000 | Vogel et al. | |
| 6,567,691 B1 * | 5/2003 | Stadler | 600/515 |
| 6,937,906 B2 | 8/2005 | Terry et al. | |
| 2003/0060849 A1 * | 3/2003 | Hsu | 607/4 |
| 2003/0109902 A1 * | 6/2003 | Girouard | 607/9 |
| 2003/0144704 A1 | 7/2003 | Terry et al. | |
| 2003/0153956 A1 * | 8/2003 | Park et al. | 607/17 |
| 2004/0171959 A1 * | 9/2004 | Stadler et al. | 600/518 |
| 2005/0192505 A1 | 9/2005 | Ostroff et al. | |
| 2006/0095083 A1 | 5/2006 | Zhang et al. | |
| 2006/0247703 A1 | 11/2006 | Gutierrez | |
| 2007/0123940 A1 | 5/2007 | Dorr et al. | |
| 2008/0154342 A1 | 6/2008 | Digby et al. | |
| 2008/0319496 A1 * | 12/2008 | Zhu et al. | 607/5 |

FOREIGN PATENT DOCUMENTS

| | | |
|---|---|---|
| DE | 102005049009 A1 | 4/2007 |
| EP | 1 302 778 A2 | 4/2003 |
| EP | 1 716 878 A1 | 11/2006 |
| WO | WO 2006124481 A2 | 11/2006 |

OTHER PUBLICATIONS

European Search Report (EP 10 15 7042), Oct. 18, 2010.
European Search Report, 09172867.5—1652/2184009, Nov. 19, 2013.

* cited by examiner

*Primary Examiner* — Carl H Layno
*Assistant Examiner* — Paula J Stice
(74) *Attorney, Agent, or Firm* — Craig A. Fieschko, Esq.; DeWitt Ross & Stevens S.C.

(57) ABSTRACT

A single-chamber heart stimulator has an electrically conductive housing, first and second detection units, and a VT/SVT discrimination unit. The first detection unit is connected to an electrode pair of a ventricular electrode lead for obtaining a first electrocardiogram signal recorded in bipolar fashion, and is designed to sense and classify ventricular heartbeats. The second detection unit is connected on one side to an electrode of the ventricular electrode lead, and on the other side to the electrically conductive housing, for obtaining a second electrocardiogram signal containing signal features characteristic of atrial heartbeats. The VT/SVT discrimination unit is connected to the first and second detection units, and effects discrimination between ventricular and supraventricular tachycardias based on ventricular heartbeats measured through the first detection unit, and on atrial heartbeats measured through the second detection unit to the extent the rate of measured ventricular heartbeats exceeds a threshold value (VT zone threshold).

22 Claims, 6 Drawing Sheets

SINGLE-CHAMBER HEART STIMULATOR

FIELD OF THE INVENTION

The invention relates to a single-chamber heart stimulator, in particular an implantable cardiac pacemaker or an implantable cardioverter/defibrillator (ICD), including a right-ventricular electrode lead. At least one right-ventricular sensing electrode and one right-ventricular stimulation electrode are attached to this electrode lead. These electrodes can be defined by a single electrode pole that then functions both as the stimulation electrode and also the sensing electrode.

BACKGROUND OF THE INVENTION

A "single-chamber heart stimulator" is generally understood to refer to a heart stimulator that is able to receive an intracardial electrocardiogram from only one ventricle via a corresponding sensing electrode, and to deliver stimulation pulses only to this ventricle via a corresponding stimulation electrode. Such stimulation and sensing electrodes can be distinct from each other, or can be formed by the same electrode pole. However, a single-chamber heart stimulator can also be a heart stimulator capable of connection to sensing electrodes in multiple ventricles, and which can therefore function as a multi-chamber heart stimulator; however, in operation, it is only connected to one electrode lead for sensing and stimulation in one ventricle.

One advantage of this type of single-chamber heart stimulator is its fundamentally simple design, coupled with the fact that only one single electrode lead has to be implanted in the heart of a patient.

Currently, multiple algorithms are known for discriminating between treatment-necessary ventricular tachycardias (VT) and supraventricular tachycardias (SVT) that do not require therapy. These kinds of algorithms are available in the implantable cardioverters/defibrillators (ICDs) of all manufacturers, and their effectiveness (sensitivity/specificity) has been demonstrated in clinical trials. However, such currently known algorithms are used in so-called two-chamber or three-chamber ICDs, since these always require information from the atrium as well.

There are various supplemental criteria for improving detection (sudden onset, stability, various QRS morphology criteria) for single-chamber ICDs, i.e., those without an implanted electrode in the atrium. In terms of the expected sensitivity/specificity, however, these criteria have limited effectiveness and are not able to distinguish all forms of VTs from SVTs. In particular, the use of morphology criteria has failed to demonstrate specificity improvement in multiple past clinical trials.

SUMMARY OF THE INVENTION

The invention involves a single-chamber heart stimulator that provides improved ventricular tachycardia (VT)/supraventricular tachycardia (SVT) discrimination. The heart stimulator has at least one partially electrically conducting housing, as well as a first detection unit (a ventricular sensing unit), a second detection unit (e.g., a far-field electrocardiogram detection unit), and a VT/SVT discrimination unit. The ventricular sensing unit (the first detection unit) is connected, or is intended to be connected, through a ventricular electrode lead to at least one ventricular sensing electrode pair to detect ventricular. This may occur, for example, by recording a first electrocardiogram signal in bipolar fashion through the ventricular sensing electrode pair and applying a process whereby QRS complexes are detected in the recorded electrocardiogram signal by a threshold comparison. The second detection unit (the far-field electrocardiogram detection unit) is connected, or is intended to be connected, on one side through a ventricular electrode lead, and the other side to the electrically conductive housing of the heart stimulator. The second detection unit is designed to detect signal features that are characteristic of atrial heartbeats (e.g., P waves) in a second electrocardiogram signal recorded through these electrodes. The VT/SVT discrimination unit is connected to the first detection unit (ventricular sensing unit) and the second detection unit (far-field electrocardiogram detection unit), and is designed to discriminate between ventricular and supraventricular tachycardias based on ventricular heartbeats measured through the first detection unit and atrial heartbeats measured through the second detection unit to the extent the rate of measured ventricular heartbeats exceeds a threshold (VT zone threshold). The second detection unit is preferably designed to detect signal features characteristic of atrial heartbeats, that is, P waves, before and during a tachycardia episode. It is also preferred that the second detection unit be designed to determine signal features characteristic of atrial heartbeats by means of signal monitoring over multiple cardiac cycles.

In order to record the second electrocardiogram, the second detection unit is preferably connected to a shock coil of the ventricular electrode lead and to the electrically conductive housing of the heart stimulator. If the ventricular electrode lead has two of these shock coils—for example, a distal shock coil intended for placement in the ventricle and a proximal shock coil intended for placement in the vena cava superior—the second detection unit can be selectively connected to one of these two shock coils and to the electrically conductive housing of the heart stimulator. The second detection unit can also be connected to a ventricular tip electrode or to a ventricular ring electrode on the ventricular electrode lead for use as a first electrode, and to the electrically conductive housing of the heart stimulator for use as the second electrode. In summary, the second detection unit preferably captures the second electrocardiogram between the electrically conductive housing of the heart stimulator, and an electrode situated on the ventricular electrode lead.

What is preferred in this regard is an approach whereby the second detection unit is connected, or intended to be connected, through a switching matrix to selectively connect to at least one of several electrodes of the ventricular electrode lead. An electrode of the ventricular electrode lead can therefore be selected in targeted fashion for connection to the second detection unit. To this end, a selection unit is preferably provided that is connected to the switching matrix and that is designed to automatically switch the switching matrix based on an EKG signal quality test in such a way that the second detection unit is connected automatically to that electrode of the ventricular electrode lead which supplies the most appropriate electrocardiogram signal.

The second detection unit can be designed to simultaneously record multiple second electrocardiogram signals, and to average them.

The single-chamber heart stimulator also preferably has a time-measuring unit that is designed to determine the time interval of successive ventricular heartbeats as the given RR interval, or its reciprocal value, as the given ventricular rate, and to supply the thus-determined value to VT/SVT discrimination unit. The VT/SVT discrimination unit is then designed to compare a given RR interval, or a given ventricular rate, with at least one VT zone threshold, and to detect a tachycardia episode if a given RR interval is shorter that the corresponding VT zone threshold, or if a given ventricular rate is greater that the corresponding VT zone threshold, and to detect a normal rhythm if the given RR interval is longer than the corresponding VT zone threshold, or if a given ventricular rate is lower than the corresponding VT zone threshold.

In an especially preferred version of the invention, the heart stimulator is capable of effecting a further discrimination of the heart rhythm by an approach wherein the discrimination unit compares a given RR interval or a given ventricular rate with at least two VT zone thresholds, and detects a tachycardia episode when the given RR interval or the given ventricular rate lies between the two VT zone thresholds. A ventricular fibrillation is detected when the given RR interval is shorter than the two VT zone thresholds, or the ventricular rate is greater than the two VT zone thresholds.

The VT/SVT discrimination unit is also preferably designed to compare signal features characteristic of atrial heartbeats, which features have been recorded both during normal rhythm and during a tachycardia episode.

Additional preferred versions of the heart stimulator are created by combining the features described above with the features noted in the following description of an exemplary version of the invention.

BRIEF DESCRIPTION OF THE DRAWINGS

A preferred exemplary version of the invention is described below with reference to the accompanying figures. Of these.

DETAILED DESCRIPTION OF AN EXEMPLARY VERSION OF THE INVENTION

Figure 1:
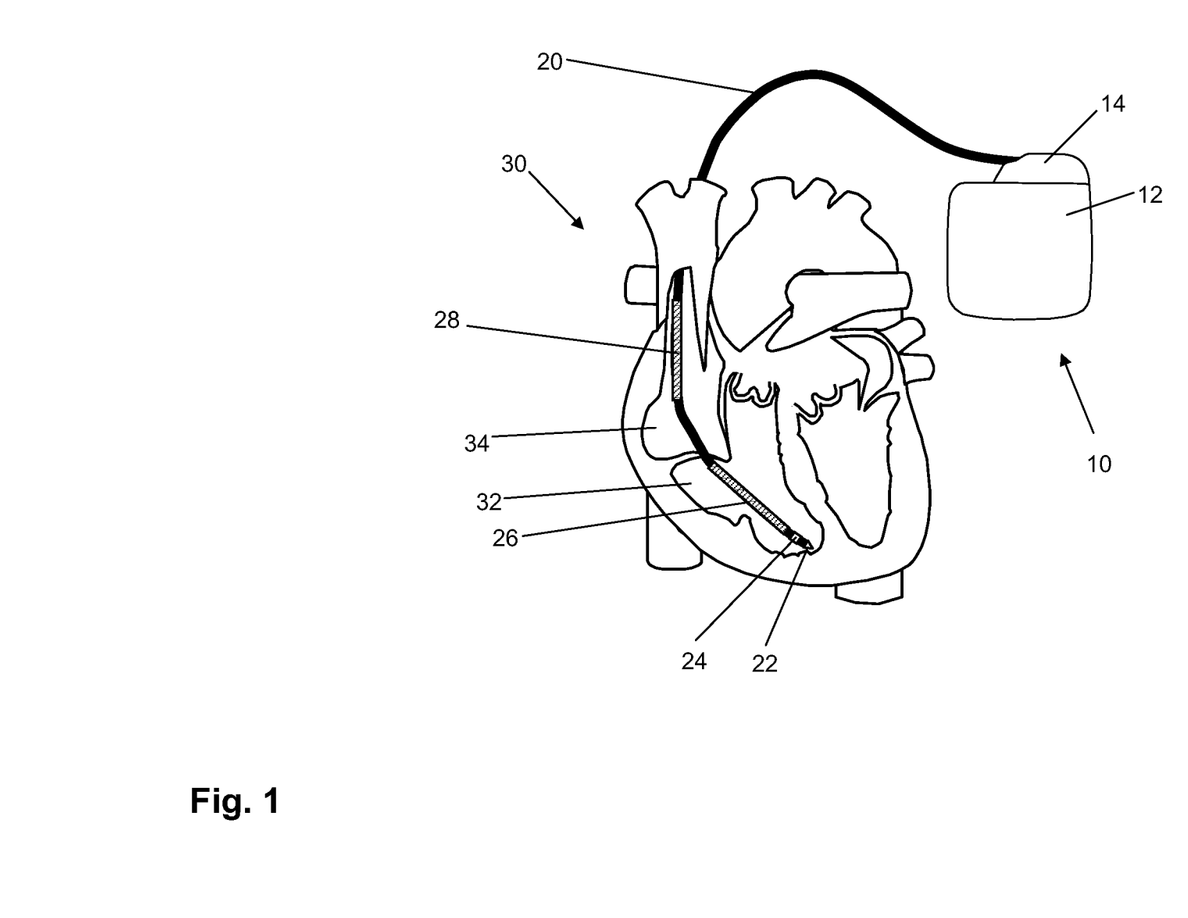
FIG. 1 illustrates a heart stimulator in the form of an implantable single-chamber cardioverter/defibrillator with electrode leads connected thereto.

FIG. 1 illustrates a ventricular heart stimulator 10 including a housing 12 and a header 14. The housing 12 is hollow, and a portion of its surface is preferably electrically conductive. Typically, the housing 12 is composed of a biocompatible metal such as titanium. A battery and electronic components of the heart stimulator 10 are located in the housing 12. The header 14 contains connection terminals, for example, for an electrode lead.

The heart stimulator 10 in FIG. 1 is connected to a flexible, implantable electrode lead 20. The illustrated electrode lead 20 is a ventricular electrode lead that at its distal end has a ventricular tip electrode 22 and a ventricular ring electrode 24 that together form a bipolar sensing and stimulation pole. Of these, the ventricular tip electrode 22 functions as the stimulation electrode. The ventricular tip electrode 22 and ventricular ring electrode 24 together form an electrode pair for bipolar sensing of ventricular events. To this end, the ventricular tip electrode 22 and ventricular ring electrode 24 are connected to a ventricular stimulation unit and a ventricular sensing unit inside the housing 12 of the heart stimulator 10 (more details are described below with reference to FIG. 2).

In addition, the ventricular electrode lead 20 has a distal ventricular shock coil, and a proximal shock coil 28. The ventricular shock coil 26 is disposed on the ventricular electrode lead 20 such that when inserted in a heart 30, the coil 36 is disposed in the ventricle 32 of the heart 30. The ventricular tip electrode 22 is then located in the apex of the ventricle 32 of the heart 30. With the ventricular electrode lead 20 implanted, the proximal shock coil 28 is located in the vena cava superior of the heart 30. No specific electrode lead is provided for stimulation of the right atrium 34 of heart 30, and similarly there is no atrial sensing electrode. The heart stimulator 20 dispenses with the need for atrial electrode leads, yet still provides the functionality of heart stimulators that are connected to an atrial electrode lead. This is explained in more detail below.

Figure 2:
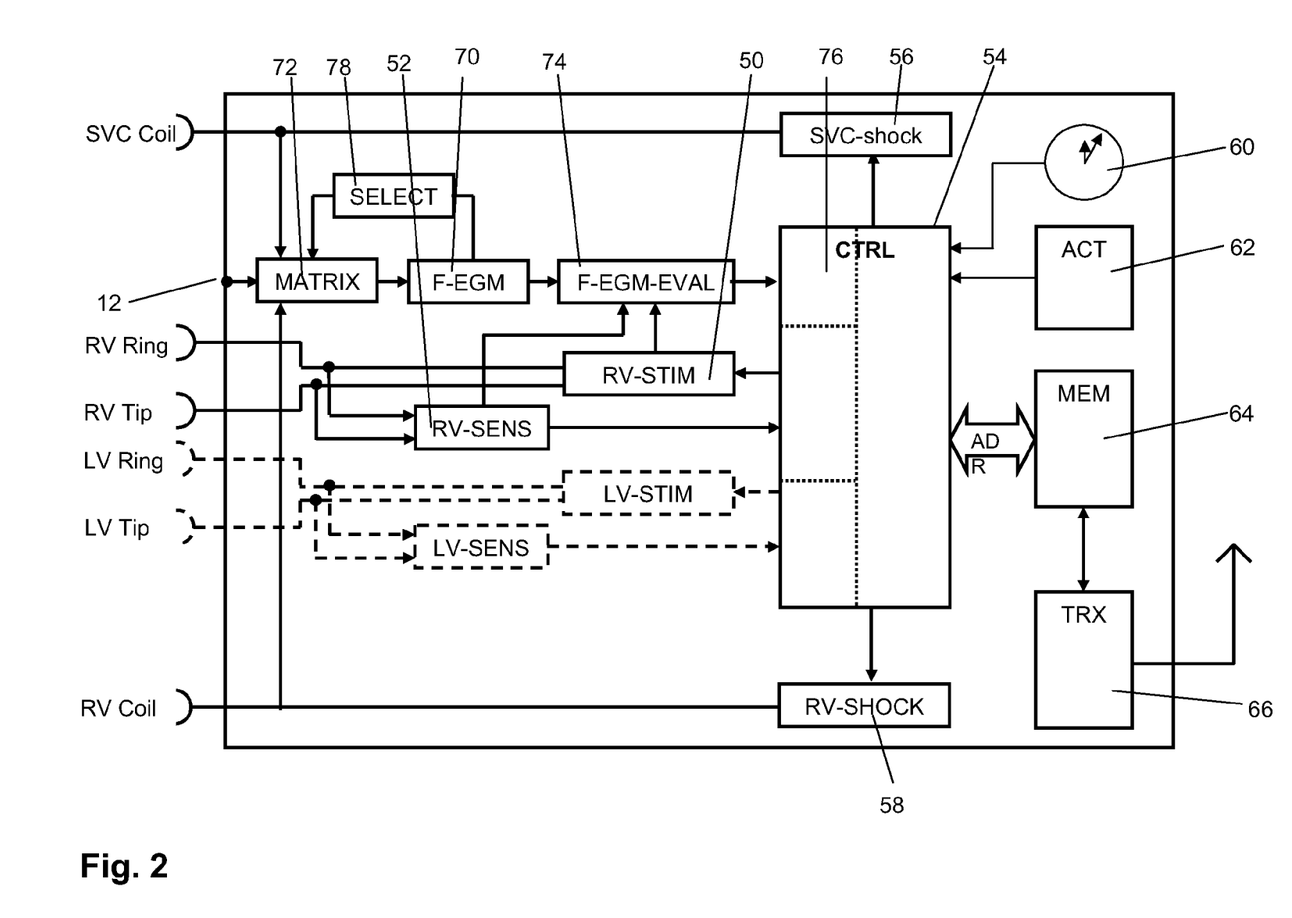
FIG. 2 is a schematic block diagram of the heart stimulator in FIG. 1.

FIG. 2 is a schematic diagram illustrating components of the heart stimulator 10 that are disposed inside the housing 12. The illustration here is not necessarily complete. In particular, some components which are not implemented in the heart stimulator 10 of FIG. 1 are shown by dotted lines.

As discussed above, heart stimulator 10 has connection contacts in its header 14 for connection to corresponding counter-contacts of an electrode lead connector plug at the proximal end of the electrode lead 20. These contacts effect the electrical connection to the electrodes of electrode lead 20. Thus the proximal shock coil 38 is connected to the terminal labeled SVC Coil in FIG. 2; the ventricular (distal) shock coil 26 is connected to the RV Coil terminal; the right-ventricular tip electrode 22 is connected to the RV Tip terminal; and the right-ventricular ring electrode 24 is connected to the RV Ring terminal. Through the RV Tip and RV Ring terminals, right-ventricular tip electrode 22 and right-ventricular ring electrode 24 are each connected respectively to a right-ventricular stimulation unit 50 and a right-ventricular sensing unit 52. At the output side, the right-ventricular sensing unit 52 is connected to a stimulation control unit 54 that in turn has an output connected to the right-ventricular stimulation unit 50. In response to a corresponding control signal, right-ventricular stimulation unit 50 is designed to generate a ventricular stimulation pulse and to deliver it at least through the RV Tip terminal.

Figure 3:
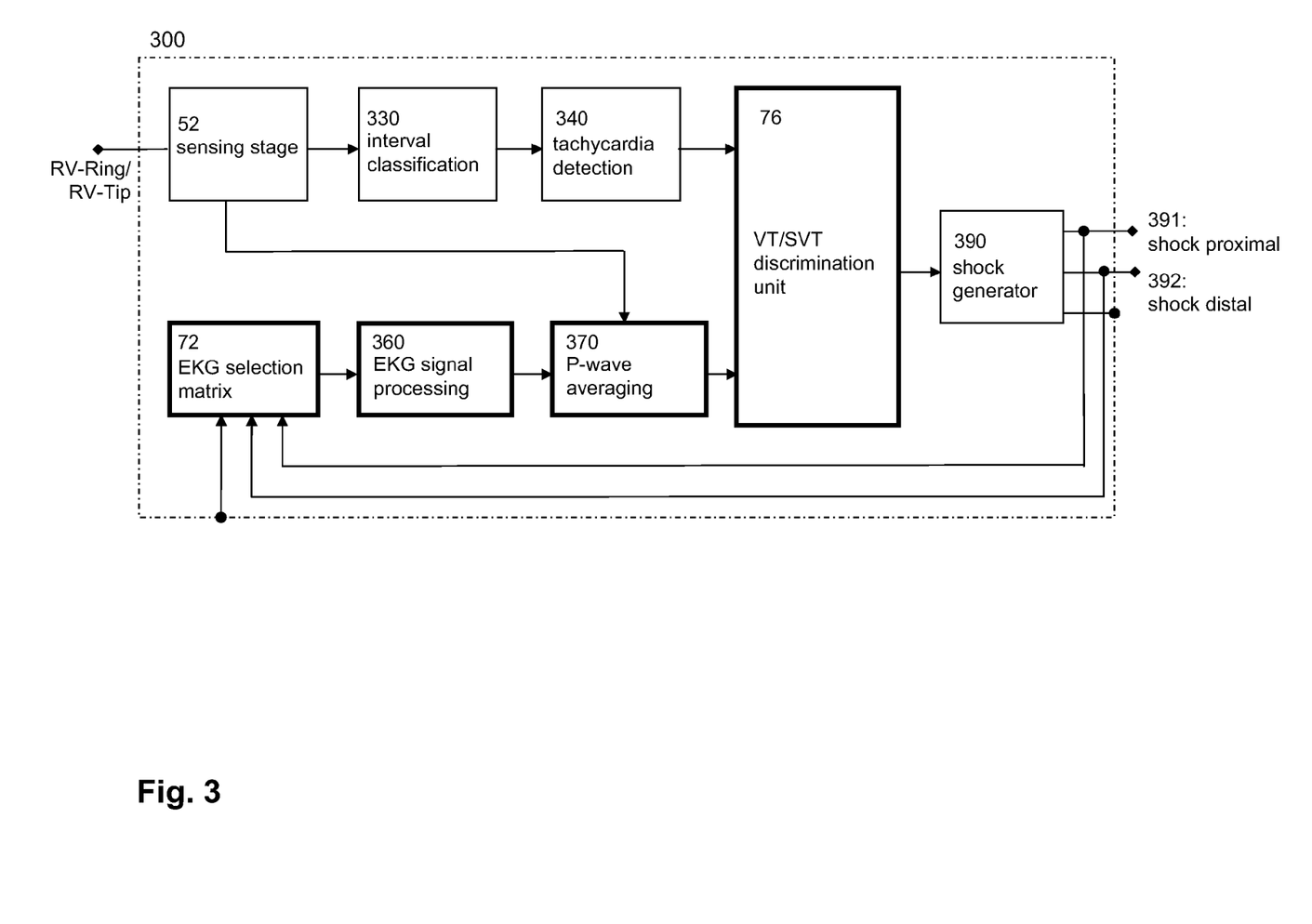
FIG. 3 is a detailed diagram illustrating the components of the heart stimulator of FIGS. 1 and 2 provided for VT/SVT discrimination.

Functions of the right-ventricular sensing unit 52 are explained in more detail below with reference to FIG. 3. The right-ventricular sensing unit 52 is designed to evaluate the characteristics of a signal resulting from the difference between potentials applied at the RV Tip and RV Ring terminals. The signal characteristics typically contain signal peaks that occur in the event of ventricular depolarizations. Depolarizations precede a contraction of the ventricular myocardium, and thus identify ventricular sensing events. These can be identified from the signal characteristics by comparing the potentials with a threshold value. This threshold value is set such that the signal peaks accompanying the ventricular depolarizations exceed the threshold value, and thus the ventricular sensing unit 52 can detect ventricular sensing events by means of a threshold comparison when the threshold value is exceeded.

In addition, defibrillation shock generators 56 and 58 are also provided to generate and deliver defibrillation shocks. The defibrillation shock generator 56 is connected through the SVC Coil terminal to proximal shock coil 28, and the defibrillation shock generator 58 is connected through the RV Coil terminal to the distal shock coil 26. The two defibrillation shock generators 56 and 58 are also each connected to the stimulation control unit 54. Additional features of the heart stimulator 10 are a timing element 60, which, for example, is utilized for interval measurement and determination of the heart rate, and an activity sensor 62 which is designed to measure the physical activity of a patient, for example, by measuring physical movement so as to enable stimulation unit 54 to adjust a stimulation rate to the physiological requirements of a patient. In addition, the heart stimulator 10 has a memory 64 to store control parameters and physiological parameters that are obtained, for example, by evaluating various signals recorded by heart stimulator 10.

Finally, the heart stimulator 10 also has a telemetry unit 66 through which heart stimulator 10 can wirelessly transmit obtained and stored physiological parameters to an external device, or, on the other hand, through which the heart stimulator 10 can receive control parameters that control the functionality of the heart stimulator 10.

The heart stimulator 10 also has a far-field electrocardiogram detection unit 70 that is connected on the input side to a switching matrix 72 through which the far-field electrocardiogram detection unit 70 is intended to be connected selectively on one side to the electrically conductive housing 12 of the heart stimulator 10, and on the other side through the SVC Coil terminal to the proximal shock coil 28, or through the RV Coil terminal to the distal shock coil 26, or through the RV Ring terminal to the right-ventricular ring electrode 24, or through the RV Tip terminal to the right-ventricular tip electrode 22. T following electrode configurations can therefore be used to attain the input signal of the far-field electrocardiogram detection unit 70:

variant A: RV-Tip (right-ventricular tip electrode 22)—housing 12 variant B: RV-Ring (right-ventricular ring electrode 24)—housing 12 variant C: RV Coil (distal shock coil 26)—housing 12 variant D: SVC Coil (proximal shock coil 28)—housing 12

Variant D is preferred when a proximal shock coil 28 is present, and variant C is preferred if no proximal shock coil 28 is present, since mapping of the atrial excitation (P wave) is generally the best in these leads.

Since multiple leads are possible for determining the P wave, use of the switching matrix 72 is preferred, wherein the matrix 72 is either manually programmable by the user, or wherein the matrix 72 automatically selects the best lead in each case for P-wave determination based on electrode impedances and signal quality. For this purpose, a selection unit 78 may be provided which evaluates the far-field electrocardiogram signals generated by the far-field electrocardiogram detection unit 70 and controls the switching matrix 72 accordingly. To this end, the selection unit 78 is connected on the input side to the far-field electrocardiogram detection unit 70 and on the output side to the switching matrix 72.

The potential difference between the selected inputs results in a far-field electrocardiogram which is collected by far-field electrocardiogram detection unit 70, amplified, converted from analog to digital, and filtered, as will be described in more detail with reference to FIG. 3. The resulting far-field electrocardiogram is then supplied from the far-field electrocardiogram detection unit 70 to an input of a far-field electrocardiogram evaluation unit 74. This far-field electrocardiogram evaluation unit 74 also has additional inputs supplied from the right-ventricular sensing unit 52 and from the right-ventricular stimulation unit 50. It is also or instead possible for the far-field electrocardiogram evaluation unit 74 to have an input supplied from the stimulation control unit 54. These additional inputs function to supply signals to the far-field electrocardiogram evaluation unit 74 which characterize ventricular sensing events or ventricular stimulation events. The far-field electrocardiogram evaluation unit 74 is designed to analyze the far-field electrocardiogram created by the far-field electrocardiogram detection unit 70 while taking into account ventricular sensing events and stimulation-event-characterizing signals in order to detect signal features in the far-field electrocardiogram that characterize atrial (sensing) events. Such signal features can be identified as P waves.

The far-field electrocardiogram evaluation unit 74 may be connected on the output side to a VT/SVT discrimination unit 76 (FIG. 3) provided as part of stimulation control unit 54. FIG. 3 illustrates components of the single-chamber heart stimulator 10 that can implement VT/SVT discrimination.

Referring back to FIG. 1, the heart stimulator 10 is connected to a right-ventricular electrode lead 20 which defines a sensing and stimulation electrode. The intracardiac electrogram derived by electrodes 22 and 24 of this electrode lead 20 is analyzed in a conventional ICD sensing stage 52 (FIG. 2), and the ventricular intervals (RR interval) are measured. These RR intervals are then classified by their cycle length in an interval classification unit 330 and assigned to at least one tachycardia zone. If an RR interval falls within a tachycardia zone, a counter is incremented accordingly in a tachycardia detection unit 340. If a specified counter criterion for tachycardia detection has been met, the VT/SVT discrimination unit 76 is activated.

The shock electrodes 26 and 28 (FIG. 1) connected to the shock generator 56/58 (FIG. 2) of the heart stimulator 10, and the electrically conductive housing 12 (FIG. 1), are also connected to the far-field EKG selection switching matrix 72/78 (FIG. 2). This selection switching matrix 72/78 determines which of the electrodes are used for the derivation of a far-field electrocardiogram signal for VT/SVT discrimination. The selection here is effected either manually as a result of programming by the physician or automatically by a signal quality analysis ("signal quality check"). The obtained far-field electrocardiogram signal is subsequently pre-processed (amplified, digitized, filtered) in an electrocardiogram signal processing unit 360 (FIG. 3), then fed to an averaging unit 370. This averaging unit performs a signal averaging that is triggered in response to a ventricular heartbeat detected by the sensing unit 52 (FIG. 2), and analyzes the electrocardiogram signal segment before the detected ventricular heartbeat in order to detect and classify a P wave as a signal feature which is characteristic of atrial heartbeats. The P wave thus detected—separated by reference P wave and P wave at the instant of tachycardia detection (tachycardia P wave)—is fed to the VT/SVT discrimination unit 76. In the VT/SVT discrimination unit 76, the rhythm is classified based on the decision tree shown in FIG. 6, which uses a comparison between the P wave recorded before the tachycardia episode and the P wave recorded during the tachycardia episode (see FIG. 5).

Figure 4:
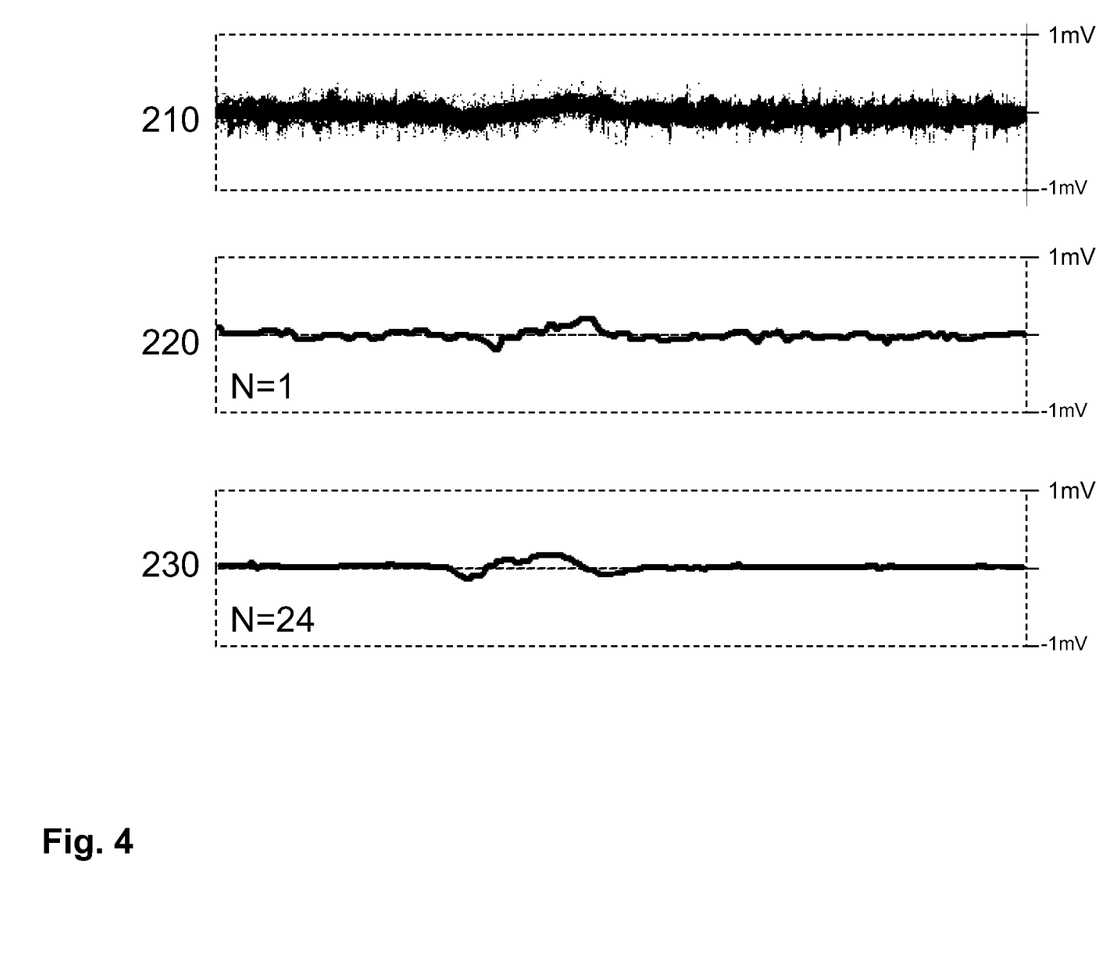
FIG. 4 illustrates the results of signal averaging to detect a P wave in the far-field electrogram.

FIG. 4 shows the results of signal averaging for the purpose of detecting a P wave in the far-field electrogram. The first/top curve (210) shows an input signal with an amplitude of 0.1 mV in order to simulate a very small P wave. In addition, the input signal is somewhat noisy so as to simulate the real conditions of the far-field EKG lead reading. In the second/middle curve (220), the lead reading of these P waves in the far-field electrogram is shown as derived by the heart stimulator 10 between the proximal shock coil 28 and the housing 12 of the heart stimulator 10. The noise signals displayed next to the P wave to be detected do not permit automatic P wave detection by the heart stimulator 10.

In the third/bottom curve (230), the signal is shown after it has been averaged over 24 cardiac cycles. This signal quality is sufficient to effect automatic detection of the P wave in the ICD.

Figure 5:
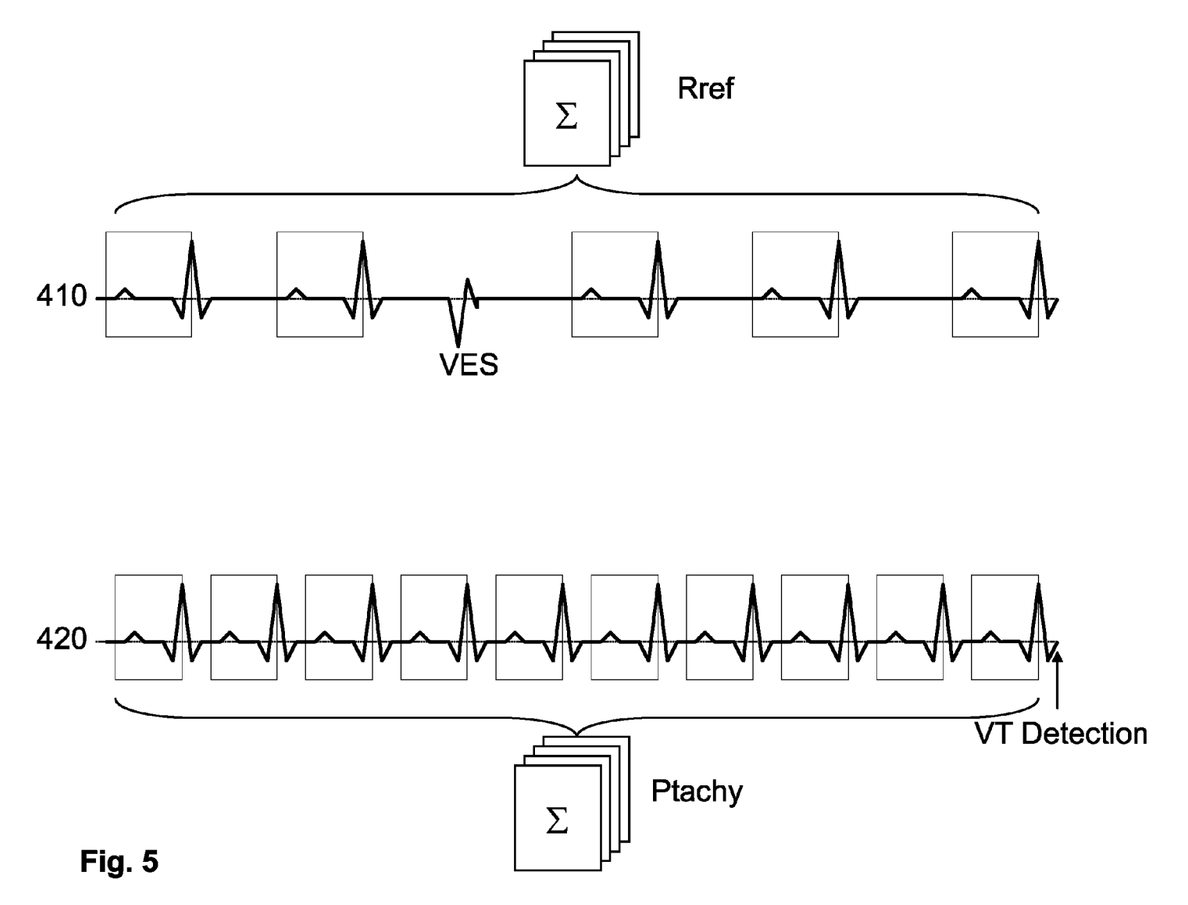
FIG. 5 illustrates a recording of a reference P wave and a tachycardia P wave.

FIG. 5 illustrates the recording of the reference P wave and the tachycardia P wave. During a heart rhythm at a frequency of less than 100 ppm (shown at 410), recording of the reference p wave is effected as a moving average determination over a specified number of intervals (e.g., the last 24 intervals) so as to always have available a current reference template for a P wave. Extra systoles (VES) or stimulated events are not incorporated in the averaging.

If a tachycardia episode is determined, the averaging is effected in a separate averaging unit for intervals within the tachycardia zone, with the result that an averaged P wave recording for VT/SVT classification is available at the time of a condition-satisfied tachycardia detection.

Figure 6:
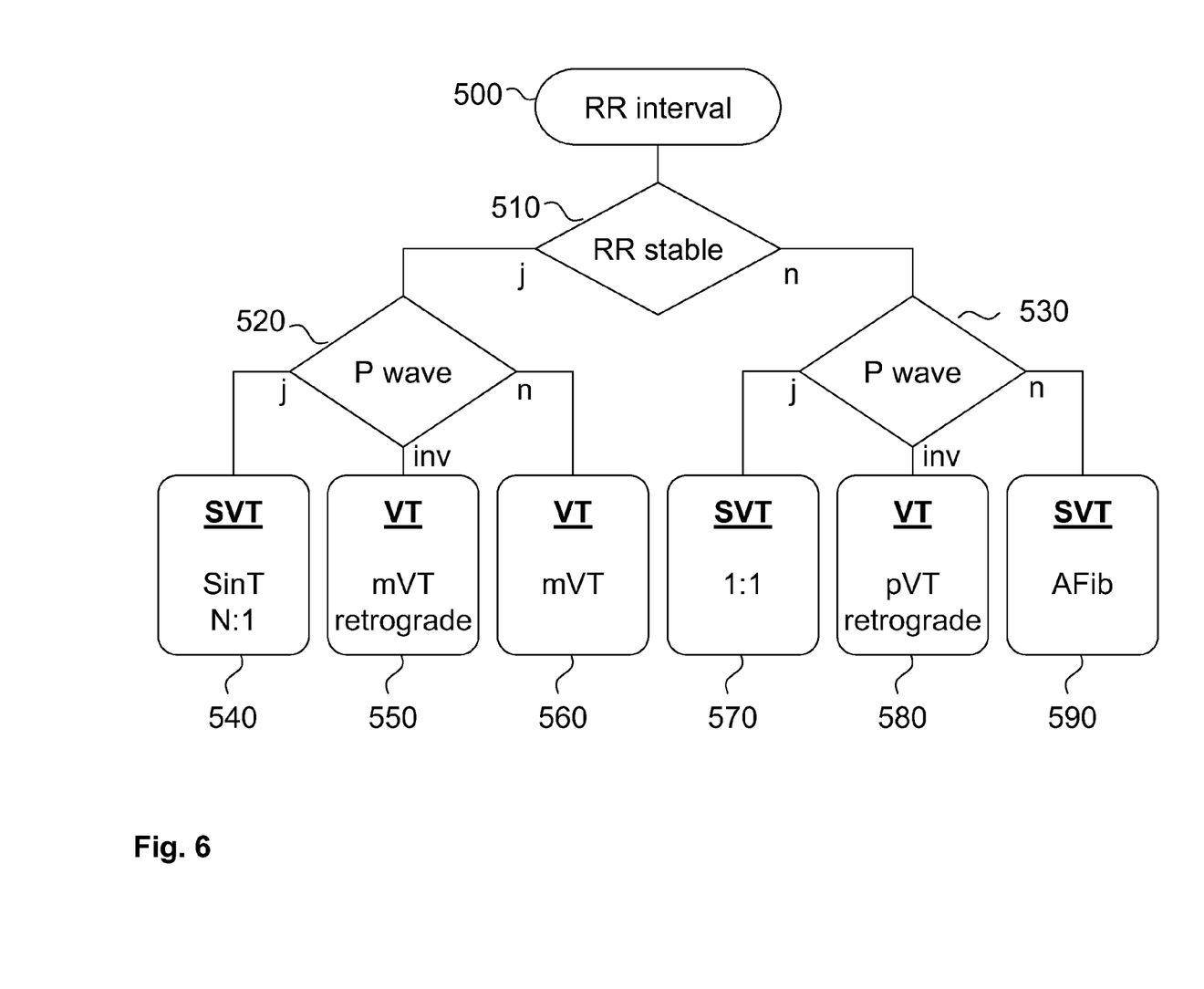
FIG. 6 is a flow diagram of an exemplary VT/SVT discrimination algorithm.

If no P wave can be determined in the reference signal, a "normal" single-chamber discrimination is implemented instead of a VT/SVT discrimination algorithm such as that shown in FIG. 6.

FIG. 6 illustrates a possible VT/SVT discrimination algorithm in the form of a flow diagram based on a P wave averaging before and during a tachycardia episode. If the detection counter reaches a count value programmed for tachycardia detection, all RR intervals (500) falling within the tachycardia zone are evaluated according to the following flow diagram:

First, a test is performed whether the tachycardia RR intervals satisfy an interval stability criterion (510). This stability test is effected using already-known methods for interval stability testing.

Once the tachycardia has been assessed as stable, a test (520) is then performed as to whether, when compared with the reference P wave (see FIG. 4), the P wave as averaged during the tachycardia episode either matches the reference P wave or is inhibited (polarity reversed) or, on the other hand, is no longer detectable.

If the averaged tachycardia P wave matches the reference, the tachycardia is assessed to be SVT. This is either a sinus tachycardia or an atrial tachycardia with a fixed conduction ratio (N:1) into the ventricle (540).

If the averaged tachycardia P wave is inhibited (polarity reversed) relative to the reference, the tachycardia is assessed as VT. This then is a monomorphic ventricular tachycardia with a retrograde conduction into the atrium (550).

If no tachycardia P wave is detectable, then the tachycardia is assessed as VT. This then involves a monomorphic ventricular tachycardia without retrograde conduction into the atrium (560).

If the tachycardia is assessed as unstable (at 510), a test (530) is then performed as to whether, when compared with the reference P wave (see FIG. 4), the P wave as averaged during the tachycardia matches the reference P wave or is inhibited (polarity reversed) or, on the other hand, is no longer detectable.

If the averaged tachycardia P wave matches the reference, the tachycardia is assessed as SVT. This then relates to an atrial tachycardia with a 1:1 conduction into the ventricle (570).

If the averaged tachycardia P wave is inhibited (polarity reversed) relative to the reference, the tachycardia is assessed as VT. This then relates to polymorphic ventricular tachycardia with a retrograde conduction into the atrium (580).

If no tachycardia P wave is detectable, the tachycardia is assessed to be SVT, relating to an atrial fibrillation with tachycardiac conduction (590). Alternatively, classification as VT can also be effected in this decision path. In this case, what would be assumed is a polymorphic VT. Since a tachycardia-conducted Afib is generally slower than a pVT, a frequency criterion can also be used to classify an SVT or VT in block 590. Alternatively, this decision can also be tied to the given VT zone: in a slow VT zone block 590 would indicate SVT, in a fast zone block 590 would indicate VT.

Since the foregoing description merely relates to exemplary preferred versions of the invention, it must be kept in mind that this patent extends not only the preferred versions discussed above, but to all versions of the invention defined in the claims below, as well as their legal equivalents.

The invention claimed is:

1. A single-chamber heart stimulator including
 a. an at least partially electrically conductive stimulator housing;
 b. a first detection unit that is:
  (1) connected to, or configured for connection to, a ventricular electrode lead, and
  (2) configured to identify signal features characteristic of ventricular heartbeats within a first electrocardiogram signal recorded through a pair of ventricular electrodes on the ventricular electrode lead which are situated solely in a ventricle;
 c. a second detection unit that is:
  (1) connected to, or configured for connection to, second electrocardiogram electrodes including:
   (a) at least one of the ventricular electrodes of the ventricular electrode lead, and
   (b) the stimulator housing,
  (2) configured to identify signal features characteristic of atrial heartbeats within a second electrocardiogram signal recorded through the second electrocardiogram electrodes;
 d. a VT/SVT discrimination unit:
  (1) connected to the first detection unit and the second detection unit, and
  (2) configured to discriminate between ventricular and supraventricular tachycardias based on both:
   (a) the ventricular heartbeats identified through the first detection unit, and
   (b) the atrial heartbeats identified through the second detection unit, whenever the rate of the identified ventricular heartbeats exceeds a threshold value.

2. The single-chamber heart stimulator of claim 1 wherein the heart stimulator delivers a stimulation shock through one or more of the electrodes on the ventricular electrode lead when a ventricular tachycardia is identified.

3. The single-chamber heart stimulator of claim 1 wherein the second detection unit is configured to identify signal features characteristic of atrial heartbeats before and during a tachycardia episode.

4. The single-chamber heart stimulator of claim 1 wherein the second detection unit is configured to identify signal features characteristic of atrial heartbeats by means of signal averaging over multiple cardiac cycles.

5. The single-chamber heart stimulator of claim 1 wherein:
 a. the ventricular electrode lead includes a shock coil thereon, the shock coil being one of the second electrocardiogram electrodes;
 b. the second detection unit is connected to, or configured for connection to, the shock coil.

6. The single-chamber heart stimulator of claim 1 wherein:
 a. the ventricular electrode lead includes a distal shock coil placed in a ventricle of the heart, the distal shock coil being one of the second electrocardiogram electrodes;
 b. the second detection unit is connected to, or configured for connection to, the distal shock coil.

7. The single-chamber heart stimulator of claim 1 wherein:
 a. the ventricular electrode lead includes a proximal shock coil placed in the vena cava superior of the heart, the proximal shock coil being one of the second electrocardiogram electrodes;
 b. the second detection unit is connected to, or configured for connection to, the proximal shock coil.

8. The single-chamber heart stimulator of claim 1 wherein:
 a. the ventricular electrode lead includes a ventricular tip electrode, the ventricular tip electrode being one of the second electrocardiogram electrodes;
 b. the second detection unit is connected to, or configured for connection to, the ventricular tip electrode.

9. The single-chamber heart stimulator of claim 1 wherein:
 a. the ventricular electrode lead includes a ventricular ring electrode, the ventricular ring electrode being one of the second electrocardiogram electrodes;
 b. the second detection unit is connected to, or configured for connection to, the ventricular ring electrode.

10. The single-chamber heart stimulator of claim 1 wherein the second detection unit is connected to a switching matrix, the switching matrix being configured to selectively connect to at least one of the electrodes of the ventricular electrode lead.

11. The single-chamber heart stimulator of claim 10:
 a. configured to apply an electrocardiogram signal quality test to second electrocardiogram signals obtained from second electrocardiogram electrodes, wherein the electrocardiogram signal quality test defines a best electrocardiogram signal; and
 b. wherein the switching matrix is configured to connect to the electrode of the ventricular electrode lead which supplies the best electrocardiogram signal.

12. The single-chamber heart stimulator of claim 1 wherein the second detection unit is configured to average multiple second electrocardiogram signals.

13. The single-chamber heart stimulator of claim 1 wherein:
 a. the heart stimulator further includes a time-measuring unit configured to:
  (1) determine an indication of the rate of ventricular heartbeats, and
  (2) supply the determined ventricular heartbeat rate indication to the VT/SVT discrimination unit,
 b. the VT/SVT discrimination unit is configured to:
  (1) compare the determined ventricular heartbeat rate indication with a VT zone threshold value, and
  (2) detect a tachycardia episode from the comparison.

14. The single-chamber heart stimulator of claim 13 wherein:
 a. the indication of the rate of ventricular heartbeats includes at least one of:
  (1) an RR interval, and
  (2) the inverse of the RR interval;
 b. the VT/SVT discrimination unit is configured to:
  (1) detect a tachycardia episode if:
   (a) the RR interval is less than, or
   (b) the inverse of the RR interval is greater than, the VT zone threshold value; and
  (2) detect a normal ventricular rhythm if:
   (a) the RR interval is greater than, or
   (b) the inverse of the RR interval is less than, the VT zone threshold value.

15. The single-chamber heart stimulator of claim 14 wherein the VT/SVT discrimination unit is configured to:
 a. compare the indication of the rate of ventricular heartbeats with at least two VT zone threshold values;
 b. detect a tachycardia episode if:
  (1) the RR interval is less than a first one of the VT zone threshold values and greater than a second one of the VT zone threshold values, or
  (2) the inverse of the RR interval is greater than a first one of the VT zone threshold values and less than a second one of the VT zone threshold values, and
 c. detect a ventricular fibrillation if:
  (1) the RR interval is less than the first and the second ones of the VT zone threshold values, or
  (2) the inverse of the RR interval is greater than the first and the second ones of the VT zone threshold values.

16. The single-chamber heart stimulator of claim 13 wherein the VT/SVT discrimination unit is configured to compare:
 a. signal features characteristic of atrial heartbeats at a normal heart rhythm, and
 b. signal features characteristic of atrial heartbeats during a tachycardia episode.

17. A single-chamber heart stimulator including
 a. a first detection unit configured to identify signal features characteristic of ventricular heartbeats within a first electrocardiogram signal recorded through a pair of electrodes on a ventricular electrode lead;
 b. a second detection unit configured to identify signal features characteristic of atrial heartbeats within a second electrocardiogram signal, the second electrocardiogram signal being a far-field electrocardiogram signal recorded through:
  (1) an electrode situated within a ventricle, and
  (2) a conductive portion of a stimulator housing from which the ventricular electrode lead extends;
 c. a VT/SVT discrimination unit configured to discriminate between ventricular and supraventricular tachycardias based on:
  (1) ventricular heartbeats identified through the first detection unit, and
  (2) atrial heartbeats identified through the second detection unit.

18. The heart stimulator of claim 17 wherein the far-field electrocardiogram signal is recorded through:
 a. a conductive portion of a stimulator housing from which the ventricular electrode lead extends, and
 b. one or more of the electrodes on the ventricular electrode lead.

19. The heart stimulator of claim 17 wherein the electrodes of the ventricular electrode lead include:
 a. one or more of a proximal shock coil and a distal shock coil, and
 b. one or more of:
  (1) a ventricular tip electrode situated on a distal tip of the ventricular electrode lead, and
  (2) a ventricular ring electrode spaced from the distal tip of the ventricular electrode lead.

20. The heart stimulator of claim 17 wherein the VT/SVT discrimination unit is further configured to discriminate between ventricular and supraventricular tachycardias whenever the rate of the identified ventricular heartbeats exceeds a threshold value.

21. A single-chamber heart stimulator including:
 a. an at least partially electrically conductive stimulator housing;
 b. a ventricular electrode lead extending from the stimulator housing, the ventricular electrode lead including at least two electrodes thereon;
 c. a first detection unit configured to identify ventricular signal features characteristic of ventricular heartbeats from signals obtained through a pair of the electrodes on the ventricular electrode lead;

d. a second detection unit configured to identify atrial signal features characteristic of atrial heartbeats from signals obtained through an electrode within a ventricle and the stimulator housing;

e. a VT/SVT discrimination unit identifying both:
  (1) ventricular tachycardias and
  (2) supraventricular tachycardias,
  on the basis of the ventricular signal features and the atrial signal features;

wherein the heart stimulator delivers stimulation shocks through one or more of the electrodes on the ventricular electrode lead when a ventricular tachycardia is identified.

22. The heart stimulator of claim 21 wherein the VT/SVT discrimination unit is further configured to identify ventricular and supraventricular tachycardias whenever the rate of the identified ventricular heartbeats exceeds a threshold value.

\* \* \* \* \*